United States Patent
Finnegan

(10) Patent No.: US 10,704,065 B2
(45) Date of Patent: Jul. 7, 2020

(54) **METHOD FOR PRODUCING 3-HYDROXYPROPANAMIDE EMPLOYING *ACETOBACTER LOVANIENSIS***

(71) Applicant: VERDANT BIOPRODUCTS LIMITED, Milton Keynes (GB)

(72) Inventor: Irene Finnegan, Milton Keynes (GB)

(73) Assignee: VERDANT BIOPRODUCTS LIMITED, Milton Keynes (GB)

( * ) Notice: Subject to any disclaimer, the term of this patent is extended or adjusted under 35 U.S.C. 154(b) by 39 days.

(21) Appl. No.: 16/072,683

(22) PCT Filed: Jan. 30, 2017

(86) PCT No.: PCT/GB2017/050232
§ 371 (c)(1),
(2) Date: Jul. 25, 2018

(87) PCT Pub. No.: WO2017/130007
PCT Pub. Date: Aug. 3, 2017

(65) Prior Publication Data
US 2018/0371511 A1    Dec. 27, 2018

(30) Foreign Application Priority Data
Jan. 28, 2016 (GB) .................................. 1601558.8

(51) Int. Cl.
*C12P 13/02* (2006.01)
*C12N 1/20* (2006.01)
*C12R 1/02* (2006.01)
*C08G 69/46* (2006.01)

(52) U.S. Cl.
CPC .............. *C12P 13/02* (2013.01); *C08G 69/46* (2013.01); *C12N 1/20* (2013.01); *C12R 1/02* (2013.01); *C12N 2500/42* (2013.01)

(58) Field of Classification Search
CPC .................................... C12R 1/02; C12P 13/02
See application file for complete search history.

(56) References Cited

U.S. PATENT DOCUMENTS 9,040,281 B2 *  5/2015  Finnegan ............. C12N 9/0008
                                                           435/243
10,131,925 B2 * 11/2018  Finnegan ................... C12P 7/62

FOREIGN PATENT DOCUMENTS

| EP | 0307926 A2 | 3/1989 |
|---|---|---|
| JP | H06225780 A | 8/1994 |
| WO | 2013180581 A1 | 12/2013 |
| WO | 2013192450 A1 | 12/2013 |
| WO | 2015118341 | 8/2015 |
| WO | WO-2015160043 A1 * | 10/2015 |
| WO | 2016027088 A1 | 2/2016 |

OTHER PUBLICATIONS

Coban et al. Effect of Various Carbon and Nitrogen Sources on Cellulose Synthesis by Acetobacter Lovaniensis HBB5; African Journal of Biotechnology, vol. 10, No. 27, pp. 5346-5354. (Year: 2011).*
Food Insight. Questions and Answers About Ammonium Hydroxide Use in Food Production, downloaded from https://foodinsight.org/questions-and-answers-about-ammonium-hydroxide-use-in-food-production/ on Oct. 31, 2019. (Year: 2009).*
Lisdiyanti et al. Systematic Study of the Genus *Acetobacter* With Descriptions of *Acetobacter indonesiensis* Sp. Nov. . . . ; Journal of General and Applied Microbiology, vol. 46, pp. 147-165. (Year: 2000).*
Schachtmann et al. Phosphorus Uptake by Plants: From Soil to Cell; Plant Physiology, vol. 116, pp. 447-453. (Year: 1998).*
International Search Report issued in Application No. PCT/GB2017/050232 dated May 4, 2017, 4 pages.
Written Opinion issued in Application No. PCT/GB2017/050232 dated May 4, 2017, 8 pages.
Dishisha et al., "Flux analysis of the Lactobacillus reuteri propanediol-utilization pathway for production of 3-hydroxypropionaldehyde, 3-hydroxypropionic acid and 1,3-propanediol from glycerol" Microbial Cell Factoris, vol. 13, No. 76, 2014, pp. 1-11.
Hannah Chung et al., "Bio-based production of monomers and polymers by metabolically engineered microorganisms" Science Direct, Current Opinion in Biotechnology, vol. 36, 2015 pp. 73-84.

* cited by examiner

Primary Examiner — Juliet C Switzer
Assistant Examiner — Paul C Martin
(74) Attorney, Agent, or Firm — Cantor Colburn LLP

(57) ABSTRACT

There is described a method for producing polymeric 3-hydroxypropionamide (3HP amide), the method comprising: culturing an *Acetobacter lovaniensis*-bacterium in a growth medium containing phosphate and ammonium, wherein culturing of the bacterium produces polymeric 3HP amide. The polymeric 3HP amide may then be hydrolysed to 3HP amide or converted to other compounds of interest.

20 Claims, 6 Drawing Sheets

| # | Cmpd.Label | RT [min] | Range [min] | Max. m/z | Area | Area % | Area Frac. % |
|---|---|---|---|---|---|---|---|
| 1 | Cmpd 1, 0.12 min | 0.12 | 0.09 - 0.15 | 0.0 | 12469.2 | 0.0 | 0.0 |
| 2 | Cmpd 2, 0.15 min | 0.15 | 0.10 - 0.18 | 452.0 | 2576629.0 | 7.7 | 1.2 |
| 3 | Cmpd 3, 0.17 min | 0.17 | 0.15 - 0.19 | 0.0 | 2208.6 | 0.0 | 0.0 |
| 4 | Cmpd 4, 2.14 min | 2.14 | 2.10 - 2.14 | 375.6 | 2231607.8 | 6.6 | 1.0 |
| 5 | Cmpd 5, 2.17 min | 2.17 | 2.14 - 2.19 | 375.7 | 3597833.9 | 10.7 | 1.6 |
| 6 | Cmpd 6, 2.25 min | 2.25 | 2.19 - 2.24 | 375.7 | 7391662.5 | 22.0 | 3.3 |
| 7 | Cmpd 7, 2.25 min | 2.25 | 2.24 - 2.26 | 375.6 | 3935454.3 | 11.7 | 1.8 |
| 8 | Cmpd 8, 2.28 min | 2.28 | 2.26 - 2.29 | 375.7 | 5481186.8 | 16.3 | 2.5 |
| 9 | Cmpd 9, 2.31 min | 2.31 | 2.29 - 2.32 | 375.7 | 9084311.5 | 27.0 | 4.1 |
| 10 | Cmpd 10, 2.34 min | 2.34 | 2.32 - 2.35 | 375.7 | 8359034.0 | 24.8 | 3.7 |
| 11 | Cmpd 11, 2.38 min | 2.38 | 2.35 - 2.40 | 375.6 | 18398752.9 | 54.7 | 8.3 |
| 12 | Cmpd 12, 2.43 min | 2.43 | 2.40 - 2.45 | 375.7 | 18716298.6 | 55.6 | 8.4 |
| 13 | Cmpd 13, 2.47 min | 2.47 | 2.45 - 2.48 | 375.7 | 14493571.8 | 43.1 | 6.5 |
| 14 | Cmpd 14, 2.50 min | 2.50 | 2.48 - 2.54 | 375.6 | 33643980.4 | 100.0 | 15.1 |
| 15 | Cmpd 15, 2.56 min | 2.56 | 2.54 - 2.56 | 375.5 | 12533957.3 | 37.3 | 5.6 |
| 16 | Cmpd 16, 2.57 min | 2.57 | 2.56 - 2.57 | 375.6 | 13016290.5 | 38.7 | 5.8 |
| 17 | Cmpd 17, 2.60 min | 2.60 | 2.57 - 2.63 | 375.7 | 31642650.7 | 94.1 | 14.2 |
| 18 | Cmpd 18, 2.65 min | 2.65 | 2.63 - 2.73 | 375.6 | 30009992.6 | 89.2 | 13.5 |
| 19 | Cmpd 19, 2.77 min | 2.77 | 2.73 - 2.87 | 255.5 | 7883365.3 | 23.4 | 3.5 |

FIG. 1 (Continued)

METHOD FOR PRODUCING 3-HYDROXYPROPANAMIDE EMPLOYING *ACETOBACTER LOVANIENSIS*

CROSS-REFERENCE TO RELATED APPLICATIONS

This Application is a U.S. National Stage Application of PCT/GB2017/050232 filed Jan. 30, 2017, which claims benefit of Great Britain Application No. GB 1601558.8 filed Jan. 28, 2016, both of which are incorporated by reference in their entireties.

FIELD OF THE INVENTION

The present invention relates to a method for producing polymeric 3-hydroxypropionamide (3HP amide) through the culture of an *Acetobacter* micro-organism under particular growth conditions. The polymeric 3HP amide can be converted to 3HP amide. The organism produces this platform molecule via the assimilation of atmospheric carbon dioxide and nitrogen. 3HP amide can be produced readily in commercial quantities. If desired, 3HP amide can be converted to a range of other commercially useful products such as acrylamide and acrylonitrile.

BACKGROUND TO THE INVENTION

A number of micro-organisms have been shown to produce 3-hydroxypropionic acid (3HP) (Andreeken, B. and Steinbuchel, A., Applied and Environmental Microbiology (2010), 76, 4919-4925). The synthesis of 3HP and other related hydroxylated carboxylic acids and polyalkanoates generally occurs under growth limiting culture conditions (Brigham C. J. et al., S3 Microbiol and Biochemical Technology (2011)). Production of hydroxyl carboxylic acids and their polymeric forms, and in particular 3HP, are of commercial significance. 3HP (CAS No. 503-66-2) can be converted to acrylic acid (CAS No. 79-10-7) on dehydration and as such is a useful platform molecule.

Previous reports of the synthesis of commercially useful amides using micro-organisms generally refer to the hydrolysis of nitriles by bacteria such as *Rhodococcus* or *Pseudomonas* species employing a nitrilase/nitrile hydratase system. Such bacterial systems are used to good effect for the synthesis of acrylamide from acrylonitrile in industrial processes (Mitsubishi process). However, de novo synthesis of acrylamide, acrylonitrile or the precursor molecule 3HP amide by a micro-organism has not been previously reported.

Two green routes to the synthesis of acrylonitrile have been reported, namely the synthesis from glycerol (V. Calvino-Casilda et al., Green Chemistry (2009), 11, 939-941) and synthesis from glutamic acid (J. Le Notre et al., Green Chemistry (2011), 13, 807-809). Synthesis from glycerol requires chemical amination, and while it represents green chemistry it is not de novo synthesis of the molecule or a precursor. The availability of glycerol from biofuel operations may be limiting and represents an issue in the debate about "food for fuel". Also synthesis from glutamic acid, which is produced by fermentation from by-products of sugar process such as vinasse (from sugar beet), may represent a larger carbon foot print than the petrochemical equivalent and be of no advantage.

WO 2013/011292 and WO 2015/118341 describe a micro-organism which is capable of producing long-chain aliphatic carboxylic acids and esters of 3-hydroxypropionic acid. These documents relate to a particular strain referred to as *Acetobacter lovaniensis* FJ1 having accession number NCIMB 41808 (deposited at NCIMB Ltd. (Ferguson Building, Craibstone Estate, Bucksburn, Aberdeen, AB21 9YA) on 12 Jan. 2011 under the provisions of the Budapest Treaty).

SUMMARY OF THE INVENTION

It has been surprisingly found that the *Acetobacter lovaniensis* strain described in WO 2013/011292 and WO 2015/118341 can produce polymeric 3HP amide. It was not previously known that this micro-organism could produce this product. This represents de novo synthesis of 3HP amide (in the form of polymeric 3HP amide). Further, this micro-organism can produce 3HP amide (in the form of polymeric 3HP amide) at commercially viable yields. This can then be converted into acrylamide and acrylonitrile.

The present invention relates to a method for producing polymeric 3HP amide using the micro-organism described in WO 2013/011292. The disclosure of WO 2013/011292 is incorporated herein in its entirety. This micro-organism has been shown to have the ability to produce polymeric 3HP amide when grown using a medium containing phosphate and ammonium.

In a first aspect, the present invention provides a method for producing polymeric 3HP amide, the method comprising: culturing an *Acetobacter lovaniensis* bacterium in a growth medium containing phosphate and ammonium, wherein culturing of the bacterium produces polymeric 3HP amide.

The synthesis of polymeric 3HP amide in the method above provides an advantage over existing technologies which require 3HP to be purified first followed by amination to yield acrylamide or acrylonitrile. Further, the polymeric 3HP amide can be generated from extremely low cost feedstocks. In addition, the route to the nitrogen containing feedstock is direct and conversion to acrylamide or acrylonitrile involves well known chemical processes.

The ability of the organism *Acetobacter lovaniensis* FJ1 to synthesise polymeric 3HP amide would appear to be unique and the organism has developed a strategy of polymerisation to obviate the toxic effects of 3HP amide itself. The production of the relatively safe polymeric precursor instead of the currently available monomeric acrylonitrile, which is a highly toxic and carcinogenic chemical, is advantageous from both an economic and a safety perspective.

The *Acetobacter lovaniensis* bacterium is cultured in a growth medium containing phosphate. The phosphate should be at an appropriate level that allows the production of polymeric 3HP amide. In some embodiments, the *Acetobacter lovaniensis* bacterium is cultured in a growth medium containing more than 1 g/litre of phosphate. 1 g/litre is the amount of phosphate ion ($PO_4^{3-}$) in the growth medium rather than the amount of the phosphate containing compound in the growth medium. For example, potassium dihydrogen phosphate ($KH_2PO_4$) has a relative molecular mass of 136. The phosphate part of this has a relative molecular mass of 95. Therefore, if 136 grams of $KH_2PO_4$ was added to 100 litres of water, there would be 1.36 g/litre of $KH_2PO_4$ in the water but there would be 0.95 g/litre of phosphate in the water.

In some embodiments, the growth medium preferably contains phosphate at a level which is more than 1.1 g/litre. In other embodiments, the growth medium contains phosphate at more than 1.2 g/litre. In further embodiments, the growth medium contains phosphate at more than 1.3 g/litre. In particular embodiments, the growth medium contains phosphate at more than 1.4 g/litre. In some embodiments, the growth medium contains phosphate at more than 1.5 g/litre. In other embodiments, the growth medium contains phosphate at more than 1.6 g-litre. In further embodiments, the growth medium contains phosphate at more than 1.7 g/litre. In particular embodiments, the growth medium contains phosphate at more than 1.8 g/litre. In some embodiments, the growth medium contains phosphate at more than 1.9 g/litre. In other embodiments, the growth medium contains phosphate at more than 2 g/litre.

In some embodiments, the growth medium contains phosphate at a level which is less than 50 g/litre. In other embodiments, the growth medium contains phosphate at less than 40 g/litre. In further embodiments, the growth medium contains phosphate at less than 30 g/litre. In various embodiments, the growth medium contains phosphate at less than 20 g/litre. In particular embodiments, the growth medium contains phosphate at less than 15 g/litre. In some embodiments, the growth medium contains phosphate at less than 10 g/litre. In other embodiments, the growth medium contains phosphate at less than 9 g/litre. In further embodiments, the growth medium contains phosphate at less than 8 g/litre. In particular embodiments, the growth medium contains phosphate at less than 7 g/litre. In some embodiments, the growth medium contains phosphate at less than 6 g/litre. In other embodiments, the growth medium contains phosphate at less than 5 g/litre. In further embodiments, the growth medium contains phosphate at less than 4 g/litre. In particular embodiments, the growth medium contains phosphate at less than 3 g/litre.

In some embodiments, the growth medium contains phosphate at a level which is between 1 and 50 g/litre. In other embodiments, the growth medium contains phosphate at between 1 and 40 g/litre. In further embodiments, the growth medium contains phosphate at between 1 and 30 g/litre. In various embodiments, the growth medium contains phosphate at between 1 and 20 g/litre. In particular embodiments, the growth medium contains phosphate at between 1 and 15 g/litre. In some embodiments, the growth medium contains phosphate at between 1 and 10 g/litre. In other embodiments, the growth medium contains phosphate at between 1 and 9 g/litre. In further embodiments, the growth medium contains phosphate at between 1 and 8 g/litre. In particular embodiments, the growth medium contains phosphate at between 1 and 7 g/litre. In some embodiments, the growth medium contains phosphate at between 1 and 6 g/litre. In other embodiments, the growth medium contains phosphate at between 1 and 5 g/litre. In further embodiments, the growth medium contains phosphate at between 1 and 4 g/litre. In particular embodiments, the growth medium contains phosphate at between 1 and 3 g/litre. In preferred embodiments, the growth medium contains phosphate at about 2 g/litre.

The phosphate containing compound in the growth medium can be any suitable compound which is soluble and which allows the bacterium to grow and produce polymeric 3HP amide. Suitable compounds include ammonium phosphates (including ammonium dihydrogen phosphate and diammonium hydrogen phosphate), sodium phosphates (including sodium dihydrogen phosphate, disodium hydrogen phosphate and trisodium phosphate), potassium phosphates (including potassium dihydrogen phosphate, dipotassium hydrogen phosphate and tripotassium phosphate), calcium phosphates (including monocalcium phosphate, dicalcium phosphate and tricalcium phosphate), magnesium phosphates (including monomagnesium phosphate, dimagnesium phosphate and trimagnesium phosphate) and phosphoric acid. The phosphate compound may be selected from ammonium phosphates (including ammonium dihydrogen phosphate and diammonium hydrogen phosphate), sodium phosphates (including sodium dihydrogen phosphate, disodium hydrogen phosphate and trisodium phosphate), potassium phosphates (including potassium dihydrogen phosphate, dipotassium hydrogen phosphate and tripotassium phosphate) and phosphoric acid. In some embodiments, the phosphate compound is an ammonium phosphate, for example, diammonium hydrogen phosphate.

The *Acetobacter lovaniensis* bacterium in cultured in a growth medium containing ammonium. It has been found that only ammonium serves to initiate the production of polymeric 3HP amide. Nitrate, nitrite and complex sources of nitrogen such as amino acids do not work. The ammonium should be at an appropriate level that allows the production of polymeric 3HP amide. In some embodiments, the *Acetobacter lovaniensis* bacterium is cultured in a growth medium containing more than 0.1 g/litre of ammonium. 0.1 g/litre is the amount of ammonium ion ($NH_4$) in the growth medium rather than the amount of the ammonium containing compound in the growth medium. For example, diammonium hydrogen phosphate (($NH_4$)$_2HPO_4$—also known as ammonium phosphate dibasic) has a relative molecular mass of 132. The ammonium part of this has a relative molecular mass of 36 (2 parts of ammonium with a relative molecular mass of 18). Therefore, if 132 grams of $(NH_4)_2HPO_4$ was added to 100 litres of water, there would be 1.32 g/litre of $(NH_4)_2HPO_4$ in the water but there would be 0.36 g/litre of ammonium in the water.

In some embodiments, the growth medium preferably contains ammonium at a level which is more than 0.15 g/litre. In other embodiments, the growth medium contains ammonium at more than 0.2 g/litre. In further embodiments, the growth medium contains ammonium at more than 0.25 g/litre. In particular embodiments, the growth medium contains ammonium at more than 0.3 g/litre. In some embodiments, the growth medium contains ammonium at more than 0.35 g/litre. In other embodiments, the growth medium contains ammonium at more than 0.4 g/litre. In further embodiments, the growth medium contains ammonium at more than 0.45 g/litre. In particular embodiments, the growth medium contains ammonium at more than 0.5 g/litre. In various embodiments, the growth medium contains ammonium at more than 0.55 g/litre. In other embodiments, the growth medium contains ammonium at more than 0.6 g/litre. In a preferred embodiment, the growth medium contains ammonium at more than 0.65 g/litre. In another preferred embodiment, the growth medium contains ammonium at more than 0.7 g/litre.

In some embodiments, the growth medium contains ammonium at a level which is less than 5 g-litre. In other embodiments, the growth medium contains ammonium at less than 4 g/litre. In further embodiments, the growth medium contains ammonium at less than 3 g/litre. In various embodiments, the growth medium contains ammonium at less than 2 g/litre. In particular embodiments, the growth medium contains ammonium at less than 1.8 g/litre. In some embodiments, the growth medium contains ammonium at less than 1.6 g/litre. In other embodiments, the growth medium contains ammonium at less than 1.4 g/litre. In further embodiments, the growth medium contains ammonium at less than 1.2 g/litre. In particular embodiments, the growth medium contains ammonium at less than 1 g/litre. In some embodiments, the growth medium contains ammonium at less than 0.9 g/litre. In other embodiments, the growth medium contains ammonium at less than 0.8 g/litre.

In some embodiments, the growth medium contains ammonium at a level which is between 0.1 and 5 g/litre. In other embodiments, the growth medium contains ammonium at between 0.1 and 4 g/litre. In further embodiments, the growth medium contains ammonium at between 0.1 and 3 g-litre. In various embodiments, the growth medium contains ammonium at between 0.1 and 2 g/litre. In particular embodiments, the growth medium contains ammonium at between 0.1 and 1.8 g/litre. In some embodiments, the growth medium contains ammonium at between 0.2 and 1.6 g/litre. In other embodiments, the growth medium contains ammonium at between 0.3 and 1.4 g/litre. In further embodiments, the growth medium contains ammonium at between 0.4 and 1.2 g/litre. In particular embodiments, the growth medium contains ammonium at between 0.5 and 1 g-litre. In some embodiments, the growth medium contains ammonium at between 0.6 and 0.9 g/litre. In other embodiments, the growth medium contains ammonium at between 0.7 and 0.8 g/litre.

The ammonium containing compound in the growth medium can be any suitable compound which is soluble and which allows the bacterium to grow and produce polymeric 3HP amide. Suitable compounds include ammonium phosphates (including ammonium dihydrogen phosphate and diammonium hydrogen phosphate), ammonium chloride, ammonium sulphate and ammonium hydroxide. Preferably, the ammonium containing compound is not ammonium iron (II) sulphate. In some embodiments, the phosphate compound is an ammonium phosphate, for example, diammonium hydrogen phosphate.

Although the bacterium can fix nitrogen from the atmosphere, a low level of nitrogen (in the form of ammonium) induces the synthesis of 3HP amide. The ratio of nitrogen to phosphorous in the growth medium is preferably between about 3:1 and about 1:3 by weight. This is the ratio between the weight of nitrogen and phosphorous atoms (not the ratio between the number of atoms). For example, if ammonium phosphate dibasic (($NH_4$)$_2$$HPO_4$) was added to the growth medium as the only source of nitrogen (in the form of ammonium) and phosphorous (in the form of phosphate), the weight ratio of nitrogen to phosphorous atoms would be about 1:1 (($NH_4$)$_2$$HPO_4$) has a molecular mass of 132 so the weight ratio of nitrogen to phosphorous atoms is 28/132 to 31/132 which equals 1:1.1). In various embodiments, the ratio of nitrogen to phosphorous in the growth medium is preferably between about 2.5:1 and about 1:2.5 by weight. In some embodiments, the ratio of nitrogen to phosphorous in the growth medium is preferably between about 2:1 and about 1:2 by weight. In other embodiments, the ratio of nitrogen to phosphorous in the growth medium is preferably between about 1.5:1 and about 1:1.5 by weight. In particular embodiments, the ratio of nitrogen to phosphorous in the growth medium is preferably about 1:1 by weight.

When cultured in a medium containing ammonium and phosphate, 3HP amide is synthesised and then assembled into short polymeric chains via a linkage similar to a peptide linkage. Typically, the polymeric 3HP amide is made up of between 2 and about 15 repeating units of 3HP amide.

The growth medium can be any suitable growth medium which allows the *Acetobacter lovaniensis* bacterium to grow and reproduce, and to produce polymeric 3HP amide. The growth medium may contain various ingredients/nutrients to allow the bacterium to grow and reproduce. The growth medium may contain one or more of the following additives: a potassium salt, a magnesium salt, a manganese salt, an iron salt, a copper salt, a cobalt salt, a sodium salt, a zinc salt, a calcium salt, a molybdenum salt, a chloride, a sulphate, a molybdate and a carbonate. These additives are generally present in the growth medium at between 0.01 and 2 g/litre.

In some embodiments, the growth medium may have one or more of the following additives in the amount specified:

| Ingredient | g/1000 ml |
| --- | --- |
| Ammonium phosphate dibasic | 1-10 g |
| Calcium Chloride | 0.1-1 g |
| Magnesium Chloride | 0.1-1 |
| Manganese Chloride | 0.01-0.1 |
| Ferric Choride | 0.01-0.1 |
| Copper Sulphate | 0.01-0.1 |
| Colbalt Chloride | 0.01-0.1 |
| Sodium Molybdate | 0.01-0.1 |
| Zinc Chloride | 0.1-1.0 |

In a particular embodiment, the growth medium has the following composition:

| Ingredient | g/1000 ml |
| --- | --- |
| Ammonium phosphate dibasic | 2.8 |
| Calcium Chloride | 1 |
| Magnesium Chloride | 1 |
| Manganese Chloride | 0.05 |
| Ferric Chloride | 0.05 |
| Copper Sulphate | 0.05 |
| Colbalt Chloride | 0.05 |
| Sodium Molybdate | 0.05 |
| Zinc Chloride | 0.5 |

The bacterium can fix carbon dioxide. Therefore, the growth medium does not require an exogenous source of carbon other than carbon dioxide dissolved in the growth medium from the atmosphere. However, in some embodiments, before the bacterium is cultured or during culturing, carbon dioxide can be bubbled through the growth medium to increase the amount of carbon dioxide dissolved in the growth medium. The bacterium can use carbon dioxide as the sole source of carbon. In some embodiments, no carbon source is present other than carbon dioxide.

The growth medium may have a pH of between about 5 and about 7. Preferably, the growth medium has a pH of about 5.5 which is optimal for the synthesis of polymeric 3HP amide.

The medium is preferably aqueous such that the nutrients/additives are dissolved in water.

The bacterium is cultured at a temperature of between 0 and 60° C. Preferably, the bacterium is cultured at a temperature of between 10 and 40° C. The optimal temperature for the synthesis of polymeric 3HP amide is about 30° C.

The bacterium may be cultured on a fixed bed consisting of a rigid support which is arranged in a reaction tank so that the layers are separated to allow air flow to the organism. The growth medium can be passed through the bed by means of a circulating pump and spray bar. Once the bed is populated by the bacterium, product can be collected in batches or continuously.

The polymeric 3HP amide is produced by culturing an *Acetobacter lovaniensis* bacterium. The bacterium can be any suitable *Acetobacter lovaniensis* bacterium which can produce polymeric 3HP amide. This includes strain FJ1 (having the accession number NCIMB 41808) and similar strains which are related to or derived from FJ1. The term "derived from" means that FJ1 can be modified or mutated to produce further bacteria. For example, genes may be inserted or removed from FJ1. Bacteria which are derived from FJ1 should be functionally equivalent to FJ1 and should be able to produce polymeric 3HP amide. Further, the derived bacterium should be able to grow under the same conditions as FJ1. Preferably, the bacterium is strain FJ1 having accession number NCIMB 41808. A bacterium can be identified as an *Acetobacter lovaniensis* bacterium by methods which are well known to those skilled in the art, for example, by using 16S rDNA analysis.

The bacterium produces polymeric 3HP amide as it grows so during culturing of the bacterium, the polymeric 3HP amide will be present in the growth medium. The polymeric 3HP amide can then be extracted, if desired.

The method may further comprise the step of separating the polymeric 3HP amide from the growth medium. This can be done in any suitable way and a number of methods will be apparent to one skilled in the art. For example, the polymeric 3HP amide can be separated using distillation, including standard distillation, fractional distillation, vacuum distillation, distillation with an entrainer, solvent extraction followed by recovery with distillation, and continuous distillation or thin film extraction. Other separation methods include membrane perfusion, electro-chemical separation, or the use of supercritical carbon dioxide. Further, separation can be done by precipitation, e.g. with calcium.

The method may further comprise the step of hydrolysing the polymeric 3HP amide to form monomeric 3HP amide. This can be done in any suitable way and a number of methods will be apparent to one skilled in the art.

Further, once the polymeric 3HP amide has been hydrolysed to monomeric 3HP amide, the method may further comprise separating the 3HP amide.

Additionally, the method may further comprise converting the polymeric or monomeric 3HP amide to 3HP acid, 3HP esters, 3-hydroxypropionamine, 3-hydroxypropionitrile, acrylamide, acrylamine, acrylic acid, allylamine, acrylonitrile, polyamine polymer, polynitrile polymer or other heteropolymers such as acrylonitrile butadiene styrene (ABS).

3HP amide monomer can be converted to 3HP acid by treatment with alkali to remove the ammonia, and to 3-hydroxypropionamine and 3-hydroxypropionitrile by reduction. Dehydration of these molecules yields acrylamide, acrylic acid, allylamine and acrylonitrile respectively. Alternatively the short chain polymeric 3HP amide, which is a repeat structure of 3HP amide linked through the carbonyl oxygen, may be reduced sequentially to give the poly-amine or poly-nitrile polymer which can then be hydrolysed to release the monomer units.

In a particular embodiment, there is provided a method for producing polymeric 3HP amide, the method comprising:
culturing *Acetobacter lovaniensis* strain FJ1 having accession number NCIMB 41808 in a growth medium containing phosphate at a level which is between 1 and 3 g-litre and ammonium at a level which is between 0.5 and 1 g/litre, wherein culturing of the bacterium produces polymeric 3HP amide.

There is provided a method for producing 3HP amide, the method comprising:
culturing an *Acetobacter lovaniensis* bacterium in a growth medium containing phosphate and ammonium, wherein culturing of the bacterium produces polymeric 3HP amide; and
hydrolysing the polymeric 3HP amide to produce 3HP amide.

DETAILED DESCRIPTION OF THE INVENTION

The invention will now be described in detail by way of example only with reference to the following figures.

OVERVIEW

Figure 1:
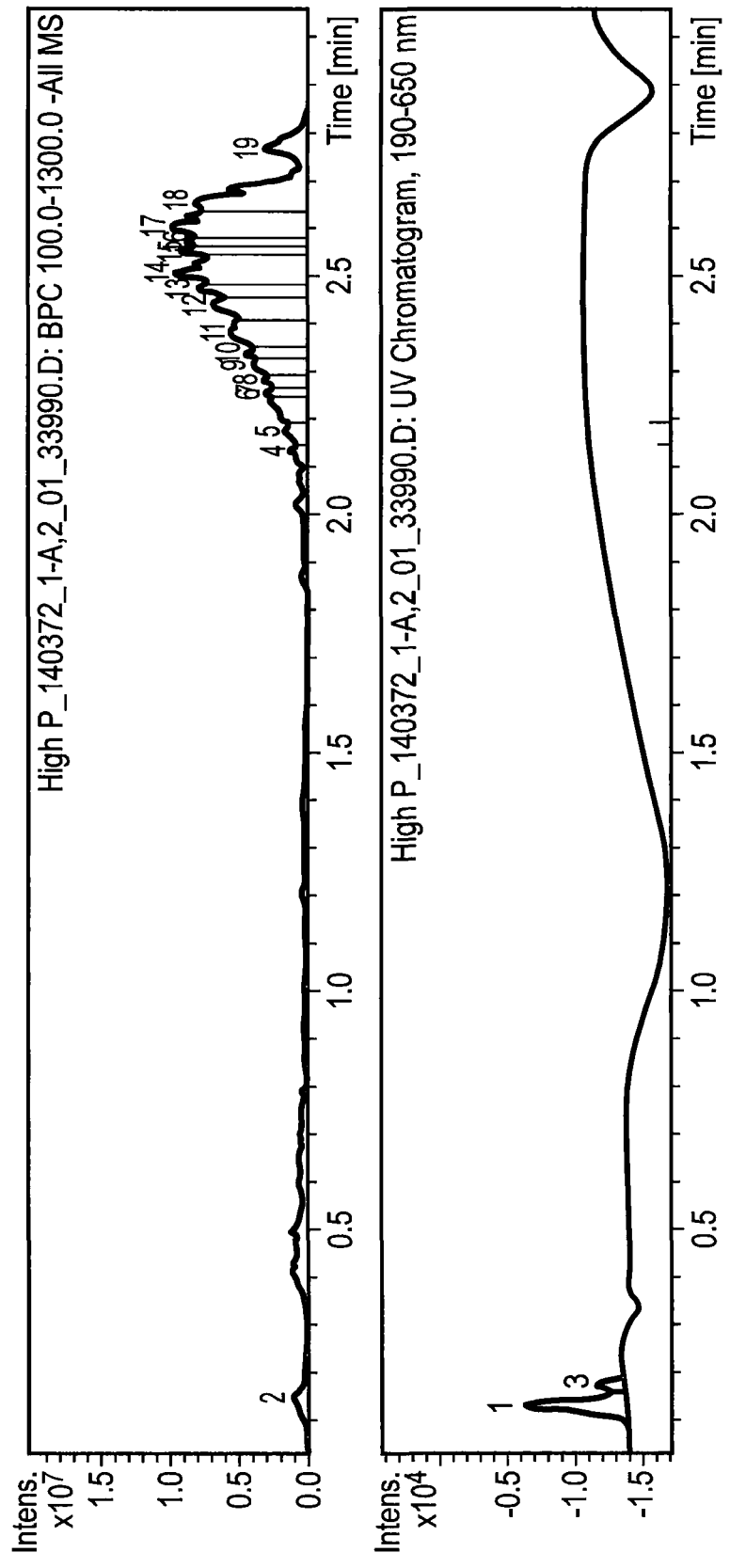
FIG. 1 is liquid chromatography-mass spectrometry spectrum (using electron spray −1) of the bacterial media. This shows a series of compounds (4 to 19) having a common fragment of mass 375.7 which represents a pentomer of 3-hydroxypropionamide.

In the presence of reduced levels of phosphate and low level of added nitrogen, *Acetobacter lovaniensis* FJ1 produces 3HP amide as a short chain polymeric material.

Without wishing to be held to a particular theory, it is though that a low level of added nitrogen may induce an enzyme system that results in the amination of 3HP post synthesis via the hydroxyl propionate cycle (Tabita, F. J. PNAS (2009) 106, 21015-21016; Strauss, G. and Fuchs. G., Eur. J. Biochem (1993), 215, 633-643). The added nitrogen does not account for the total output of nitrogen in the form of 3HP amide which is minimally 10 times higher in the final product and suggests that nitrogen fixation is not suppressed by an added source of nitrogen. The effect is specific to ammonium containing salts, and nitrates and nitrites have been shown not to be effective. The fixation of nitrogen by this organism via a nitrogenase enzyme type complex results in the generation of hydrogen (Tamagnini P. et al., Microbiology and Molecular Biology Reviews (2002), 66, 11-20) which is used by the organism's hydrogenase enzyme system and balances out the redox system of the organism. While carbon and nitrogen assimilation have been noted in other organisms (Levican G. et al., BMC Genomics (2008) 581 1186; Dubbs J. M. and Tabita F. R. Ferns Microbiol Rev (2004) 28, 353-356; McKinlay J. B. and Harwood C. S., PNAS (2010), 1073, 1-7), the use of carbon dioxide fixation as a redox recycling mechanism has only been previously noted in anoxygenic phototrophic bacteria such as non-sulphur bacteria where the carbon dioxide is reduced via the Calvin Benson Basham cycle. *Acetobacter* species may be able to take advantage of this effect. While not having a functioning Calvin Benson Basham cycle, they do retain genetic elements of it, or the 3HP cycle is used to the same effect. Further to this, a proton motive force dependent efflux system for 3HP may operate as seen in *Acetobacter aceti* (Matsushita K. et al., Bacteriol. (2005), 187, 4346-4352).

The synthesis of 3HP amide has not been noted in any bacteria capable of the synthesis of 3HP. Although lacking direct proof, it may be linked to the ability to concurrently fix nitrogen as well as carbon. The 3HP amide would appear to assemble into short lengths of polymeric material and this enables the product to be collected in a safe form prior to conversion to either acrylamide, acrylonitrile or acrylic acid. The product can be collected by evaporation to remove the water, distillation at atmospheric pressure to concentrate the product in the stillage, vacuum distillation at 40° C. and 50 mBa, precipitation with calcium or zinc salts, extraction with a suitable solvent, or adsorption chromatography.

Process for Producing 3HP Amide—CAS Number 2651-43-6

*Acetobacter lovaniensis* FJ1 is grown on minimal salt media in which a source of nitrogen, specifically as an ammonium salt, is included and in which the ratio of nitrogen to phosphorous is about 1:1 by weight. The composition of the media is shown in the table below:

TABLE 1

Composition of Minimal Salt Media Used to Grow *Acetobacter lovaniensis* FJ1

| Ingredient | g/1000 ml |
|---|---|
| Ammonium phosphate dibasic | 2.8 |
| Magnesium chloride | 1.0 |
| Calcium chloride | 1.0 |
| Manganese chloride | 0.05 |
| Ferric chloride | 0.05 |
| Copper sulphate | 0.05 |
| Colbalt chloride | 0.05 |
| Sodium molybdate | 0.05 |
| Zinc chloride | 0.50 |

The media is dissolved in water and filtered. The water used can either be distilled water or tap water. The micro-organism can be grown under non-sterile conditions.

The micro-organism is grown in a fixed trickle down reactor consisting of a fixed but porous bed of an inert material such as polyurethane foam or wood chips. The inert bed is supported on trays or other suitable containers in a reactor vessel. The reactor vessel comprises a tank to support the bed, a sump to collect product, and a circulating pump at the bottom of the sump to circulate media from the sump back to the top of the reactor via a spray bar. Air is forced into the bottom of the bed using a centrifugal air pump.

The micro-organism is inoculated into 2 litre quantities of media in shake flasks or other suitable containers and grown to an A600 of between 0.75 and 1.00. Two litres of media is then diluted in fresh media to a volume of 10 litres and again cultured to an A600 of between 0.75 and 1.00. The volume of the culture media is increased to the desired volume by repeated splitting of the culture. This media is them applied to the bed at the top and allowed to trickle down. The media is circulated until the A600 in the sump drops to below 0.1 indicating that the bacteria have fixed to the bed. The bed is then further circulated for a period of seven days with a 10× concentrate of minimal salt media to allow the bed to populate. At the end of the growth period the minimal salt media is decreased to the concentration shown in Table 1, to maintain growth and allow the organism to carry out bio-transformations. The A600 of the material in the sump is monitored to ensure that the organism remains fixed to the bed. The temperature of the bed is maintained at 30° C. using a heat exchanger linked to the circulation of the media.

The product is collected from spent media in the sump. The spent media can be removed in batches or on a continuous basis. The poly 3HP amide can be collected by precipitation with calcium or zinc salts, concentrated by distillation either at atmospheric pressure or under vacuum, membrane perfusion, solvent extraction, adsorption or the use of critical carbon dioxide.

Recoveries are measured after various pre-purification methods which include concentration or precipitation with calcium or zinc salts. Following this step the material is acidified to pH 2.0 and a suitable catalyst added to effect hydrolysis of the poly 3HP amide to monomeric 3HP amide. Typically the sample is acidified to pH 2.0 with either concentrated sulphuric acid or concentrated hydrochloric acid. Hydrogen peroxide is added to a final concentration of 2.0% and the sample heated in a suitable vessel at 100° C. for 30 minutes to one hour under reflux. This effects hydrolysis of the polymeric material to monomer units which can then be measured using high pressure liquid chromatography. Typically the 3HP amide can be eluted isocratically using a 25 cm ODS-H, 4.6 mm column with a mobile phase of 90% ethanol and 10% water. Flow rates of 0.3 ml/min and a column temperature of 40° C. are employed. Identification and quantification can be made relative to a standard which can be obtained from Sigma Aldrich.

The polymeric material can be identified using LC-mass spectroscopy with either electron spray +1 or electron spray −1. The polymer presents as a series of short chains of up to 12 repeats in both the media, concentrated media and material prepared from the hydrolysis of calcium precipitate. In the example shown of electron spray −1 analysis of bacterial media (FIG. 1), a series of compounds show a common fragment of mass 375.7 representing a pentomer of 3HP amide. The polymer presents both as repeats of 3HP amide and also acrylamide which may be the result of dehydration of the polymer during preparation. NMR of calcium precipitated polymer and polymer concentrate are indicative of material containing an acrylic like molecule, but lacking the typical feature of C=O at around 12 ppm. The polymeric material can be hydrolysed back to monomer units and analysed by HPLC; the 3HP amide standard and sample material co-run on the column. When material generated from hydrolysis of concentrated media or calcium precipitate is further heated with sodium hydroxide, ammonia is released and 3-hydroxypropionic acid is generated.

Figure 2:
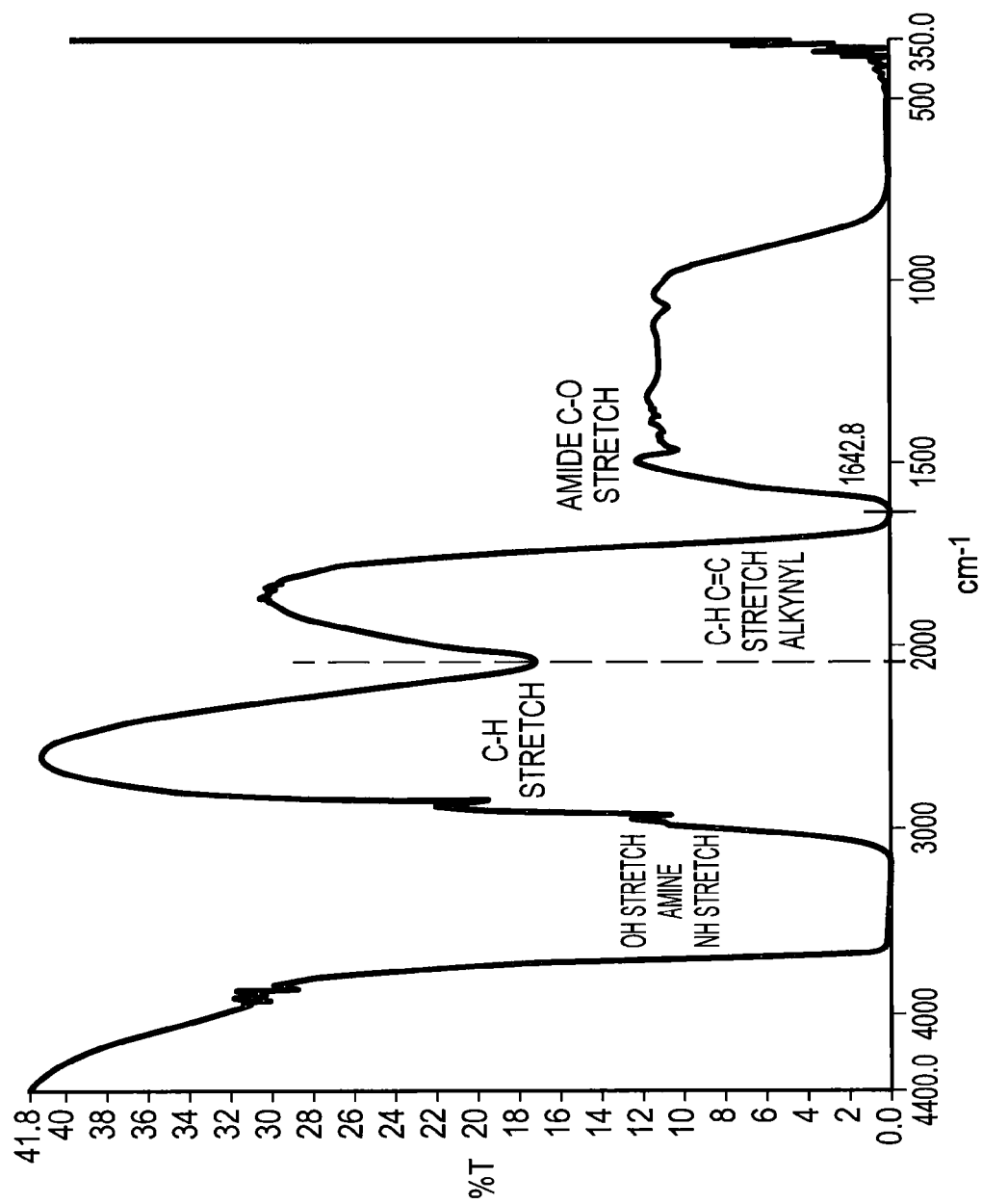
FIG. 2 is an infra-red spectrum of the 3-hydroxypropionamide monomer.
Figure 3:
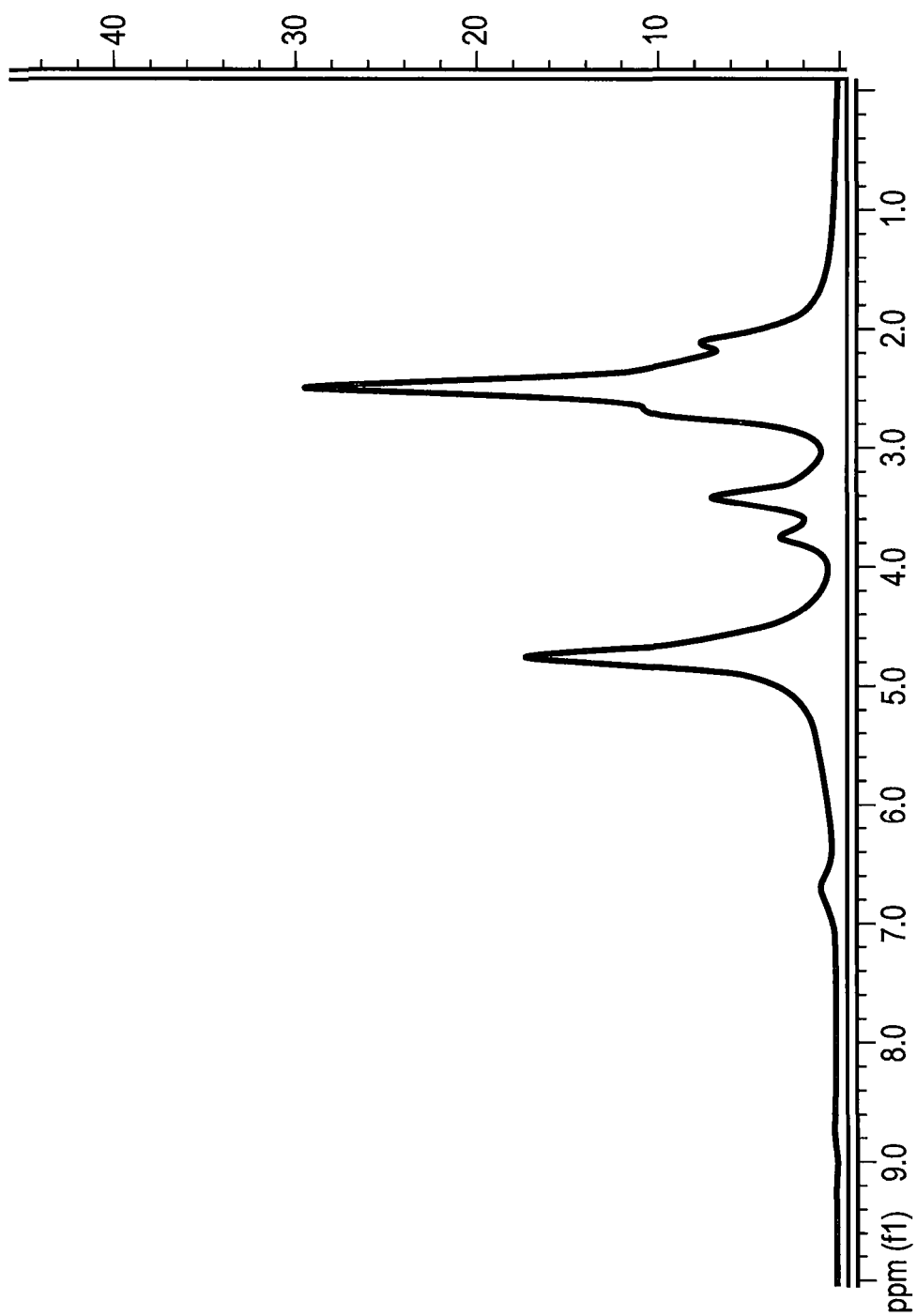
FIG. 3 is a 1H NMR spectrum of the 3-hydroxypropionamide monomer.
Figure 4:
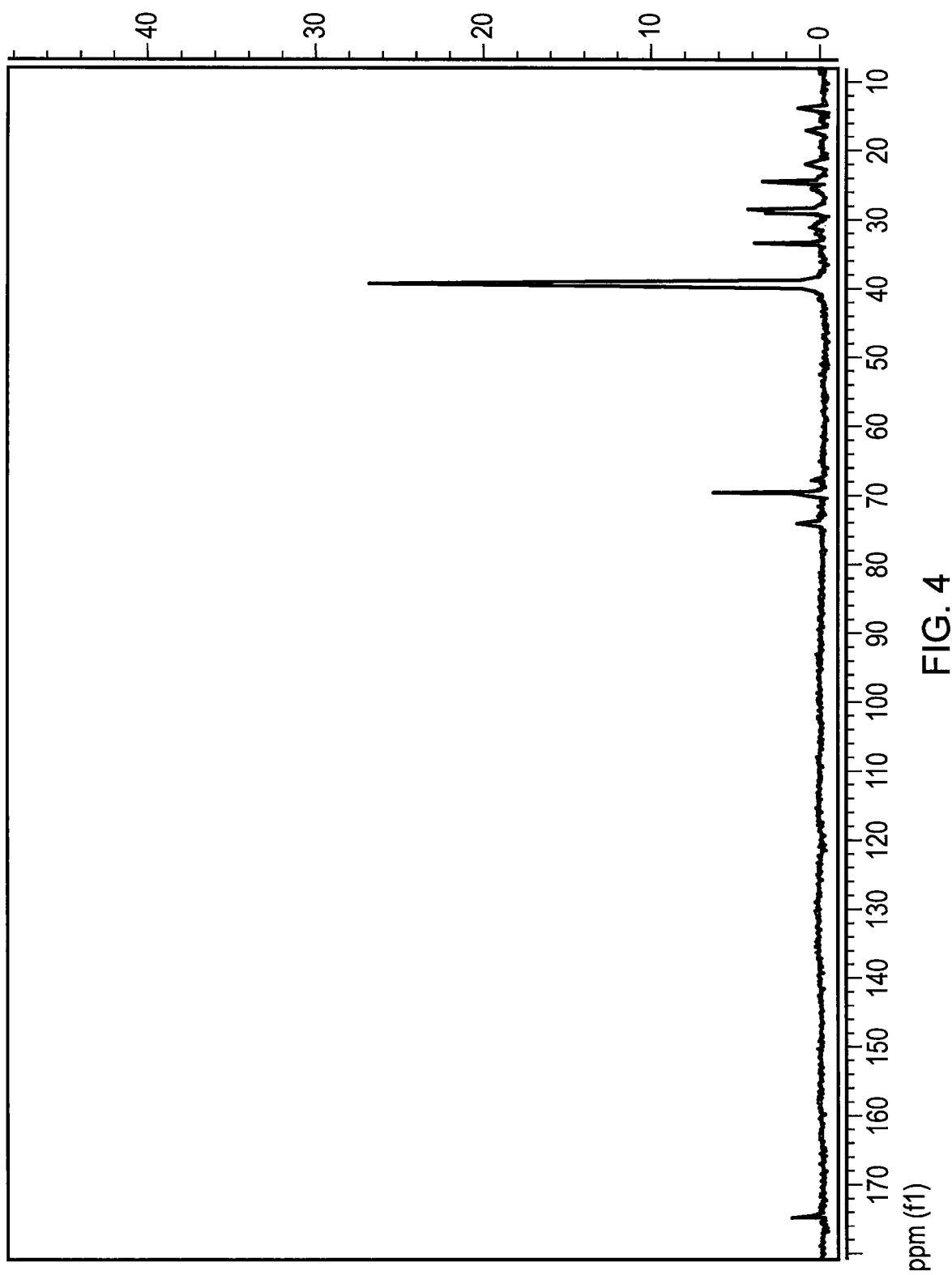
FIG. 4 shows a 13C NMR spectrum of the 3-hydroxypropionamide monomer.
Figure 5:
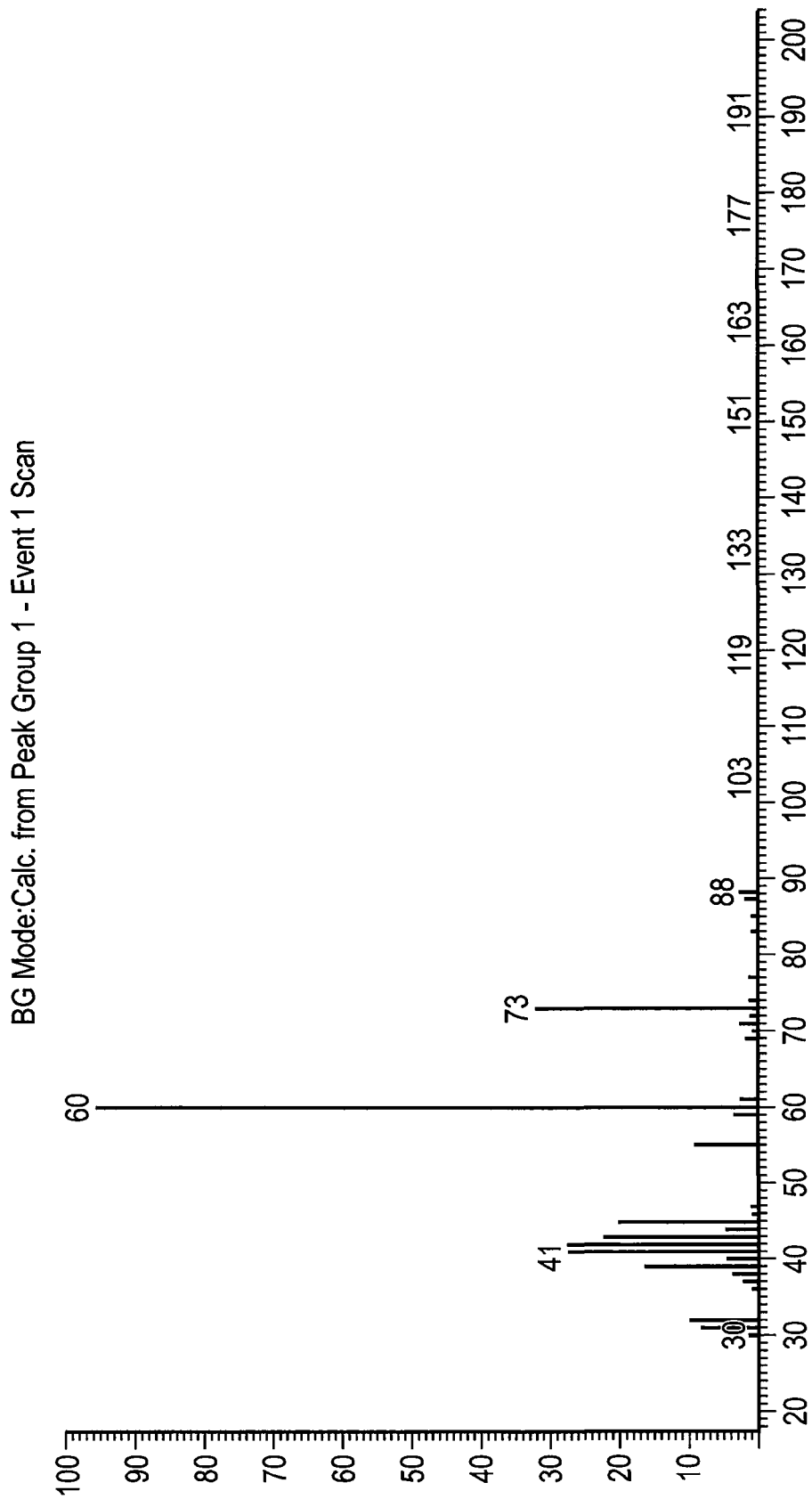
FIG. 5 shows a gas chromatography-mass spectrometry spectrum of the 3-hydroxypropionamide monomer.

Amides can be identified by various techniques. Infra-red (FIG. 2) shows the typical presence of low frequency C=O at 1660 $cm^{-1}$ and N—H stretches at 3500 $cm^{-1}$ and 3100 $cm^{-1}$ (two for $NH_2$ and one for NH). 1H NMR gives broad exchangeable signals between 5-8 ppm for NH and from 2-2.4 for H—C—C—O (FIG. 3). 13C NMR typically gives a signal between 160-180 ppm for C=O (de-shielding due to O) and minimal intensity signals characteristic of C's with no attached H's (FIG. 4). Both the 1H NMR spectrum and 13C spectrum match that of a known standard. UV-visible spectra show an absorption maxima at around 215 nm from the O lone pair of electrons and the anti-bonding C=O. Mass spectroscopy is typical of an amide (FIG. 5).

EXAMPLES

Example 1: The Growth of the Organism in the Presence of an Added Ammonium Salt

When grown on a fixed bed, poly 3HP amide can be collected from the sump in batches withdrawn at 24 hour intervals. Using a test bed with a volume of 1 $m^3$, a sump volume of 200 litres, a temperature of 30° C., a starting media pH of 5.5, the organism achieves levels of production of between 30 and 50 g/l. Using HPLC, the standard is retained at 9.308 minutes and the sample at 9.294 minutes following hydrolysis of the polymeric 3HP amide material. A yield of 4.95% or 49.5 g/l was achieved, which is equivalent to approximately 2 g/l/h. A 3HP standard was retained at 8.973 minutes and did not match that of the hydrolysed material.

Example 2: Synthesis of Acrylamide from 3HP Amide

The spent bacterial media is harvested and concentrated by one of the methods detailed above or collected as a calcium precipitate. The concentrated media or calcium precipitate is then hydrolysed by acidification with concentrated hydrochloric acid or concentrated sulphuric acid to a pH of 2.0. A suitable catalyst is then used to hydrolyse the polymeric 3HP amide material present back to monomeric units. The material generated is further concentrated and dehydrated. Dehydration results in the generation of acrylamide. The acrylamide generated can further be reduced to an amine using a suitable catalyst system. For example, 1,1,3,1,tetramethyl siloxane and 1,2-bis(dimethylsilyl) benzene are effective reducing agents for platinum catalysts (S. Hanada, E. Tsutsumi, Y. Motoyama, H. Nagashima, J. Am. Chem. Soc 2009, 131, 15032-15040). Activation with Tf2O followed by reduction with sodium borohydride in THF at room temperature (S.-H. Xiang, J. Xu, H.-Q. Yuan, P.-Q. Huang Synlett. 2010, 1829-1832).

Example 3: Synthesis of Acrylonitrile from 3HP Amide

The 3HP amide can be dehydrated to the nitrile using N,N-dihydro-C-oxo-bi elimination (Acrylamide/Polyacrylamide: Overview of the Chemistry (1988) pp 9, C. G. Daughton). Phosphorous pentoxide can be used as a dehydrating agent although acid halides or anhydrides can also be used.

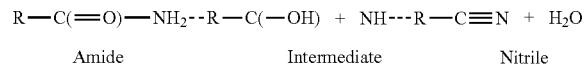

Amide      Intermediate      Nitrile

Alternatively, the primary amine generated in example 2 can further be converted to acrylonitrile with trichloroisocyanuric acid (F.-E. Chen, Y.-Y. Kuang, H.-F. Dai, L. Lu, M. Huo, Synthesis 2003, 2629-2631) under mild oxidative conditions. Alternatively, the primary amine can be converted directly to the nitrile under non-oxidising conditions using a ruthenium complex catalyst (K.-N. T. Tseng, A. M. Rizzi, N. K. Szymczak, J. Am. Chem Soc. 2013, 135, 16352-16355; O. D. Pavel, P. Goodrich, L. Cristian, S. M. Coman, V. I. Parvulescu and C. Hardacre, Catal. Sci. Technol. 2015, 5, 2696-2704).

Example 4: Synthesis of Acrylamine from 3HP Amide

The amide form can be reduced to the amine using metal hydrides such as $LiAlH_4$ or $BH_3$. Nitriles are intermediates in the reduction of unsubstituted amides. In diglycol methyl ether, primary amides can be quantitatively reduced and stopped at the nitrile. Other reducing agents that can be used to the same effect are Vitride $((NaAlH_2(OCH_2CH_2OCH_3)_2)$, borane tetrahydrofuran $(BH_3.THF)$, borane methyl sulphide $((CH_3)2S:BH_3))$.

Example 5: Synthesis of 3HP Acid from 3HP Amide

The 3HP amide can be converted to 3HP, the acid form by heating in the presence of a dilute solution of sodium hydroxide to release ammonia.

Example 6: Synthesis of Acrylic Acid from 3HP

Acrylic acid can be generated from 3HP by dehydration using one of the techniques detailed in previous patents such as WO 2013/192451 or U.S. Pat. No. 8,846,353.

Example 7: Synthesis of 3HP Esters from Calcium Precipitate

3HP esters such as methyl 3-hydroxypropionic acid can be generated by direct methylation of the calcium precipitated or concentrated polymer. The precipitate or concentrate is reacted with methanol in the presence of sulphuric acid as catalyst. The reaction mixture is heated to 60° C. for 60 minutes and the methylated ester collected by distillation.

The invention claimed is:

1. A method for producing polymeric 3-hydroxypropionamide (3HP amide), the method comprising:
    culturing an *Acetobacter lovaniensis* bacterium having accession number NCIMB 41808 in a growth medium containing phosphate and ammonium,
    wherein culturing of the bacterium produces polymeric 3HP amide,
    wherein the method further comprises a step of separating the polymeric 3HP amide from the growth medium.
2. The method of claim 1, wherein the growth medium contains ammonium at more than 0.1 g/litre.
3. The method of claim 1, wherein the growth medium contains ammonium at more than 0.5 g/litre.
4. The method of claim 1, wherein the growth medium contains ammonium at between 0.5 and 1 g/litre.
5. The method of claim 1, wherein the growth medium contains phosphate at more than 1 g/litre.
6. The method of claim 1, wherein the growth medium contains phosphate at more than 1.5 g/litre.
7. The method of claim 1, wherein the growth medium contains phosphate at between 1 and 3 g/litre.
8. The method of claim 1, wherein the growth medium contains phosphate at between 1 and 3 g/litre and ammonium at between 0.5 and 1 g/litre.
9. The method of claim 1, wherein the ratio of nitrogen to phosphorous in the growth medium is between about 2:1 and about 1:2 by weight.
10. The method of claim 1, wherein the growth medium does not contain an exogenous source of carbon.
11. The method of claim 1, wherein the growth medium has a pH of between 5 and 7.
12. The method of claim 1, wherein the bacterium is cultured at a temperature of between 10° C. and 40° C.
13. The method of claim 1, wherein the method further comprises a step of hydrolysing the polymeric 3HP amide to form monomeric 3HP amide.
14. The method of claim 13, wherein the method further comprises a step of separating the monomeric 3HP amide.
15. The method of claim 13, wherein the method further comprises converting the monomeric 3HP amide to other compounds.
16. The method of claim 13, wherein the method further comprises converting the monomeric 3HP amide to 3HP acid, 3HP esters, 3-hydroxypropionamine, 3-hydroxypropionitrile, acrylamide, acrylamine, acrylic acid, allylamine, acrylonitrile, polyamine polymer, polynitrile polymer or other heteropolymers such as acrylonitrile butadiene styrene (ABS).
17. The method of claim 1, the method comprising:
    culturing *Acetobacter lovaniensis* strain FJ1 having accession number NCIMB 41808 in a growth medium containing phosphate at a level which is between 1 and 3 g/litre and ammonium at a level which is between 0.5 and 1 g/litre,
wherein culturing of the bacterium produces polymeric 3HP amide.

18. The method of claim 1, wherein the method further comprises converting the polymeric 3HP amide to other compounds.

19. The method of claim 1, wherein the method further comprises converting the polymeric 3HP amide to 3HP acid, 3HP esters, 3-hydroxypropionamine, 3-hydroxypropionitrile, acrylamide, acrylamine, acrylic acid, allylamine, acrylonitrile, polyamine polymer, polynitrile polymer or other heteropolymers such as acrylonitrile butadiene styrene (ABS).

20. A method for producing 3HP amide, the method comprising:
culturing an *Acetobacter lovaniensis* bacterium having accession number NCIMB 41808 in a growth medium containing phosphate and ammonium, wherein culturing of the bacterium produces polymeric 3HP amide; and
hydrolysing the polymeric 3HP amide to produce 3HP amide.

* * * * *